(12) United States Patent
Miller et al.

(10) Patent No.: US 9,049,919 B2
(45) Date of Patent: Jun. 9, 2015

(54) TOOTHBRUSH WITH A BRISTLE FIELD WHICH COMPRISES A COMPOSITE OF LAYERS OF BASE AND BRISTLE COMPONENTS

(71) Applicant: KONINKLIJKE PHILIPS N.V., Eindhoven (NL)

(72) Inventors: Kevin Arnold Miller, Bellevue, WA (US); Folkert Vrijburg, Drachten (NL); Geert Hendrik Westrup, Sint Jansklooster (NL); Jurriaan Bernhard Rudolf Leveling, Emmen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/366,760

(22) PCT Filed: Dec. 27, 2012

(86) PCT No.: PCT/IB2012/057755
§ 371 (c)(1),
(2) Date: Jun. 19, 2014

(87) PCT Pub. No.: WO2013/098776
PCT Pub. Date: Jul. 4, 2013

(65) Prior Publication Data
US 2014/0345070 A1    Nov. 27, 2014

Related U.S. Application Data

(60) Provisional application No. 61/580,354, filed on Dec. 27, 2011.

(51) Int. Cl.
| | | |
|---|---|---|
| *A46B 7/06* | (2006.01) | |
| *A46B 9/08* | (2006.01) | |
| *A46B 13/02* | (2006.01) | |
| *A46B 3/00* | (2006.01) | |
| *A46B 9/04* | (2006.01) | |
| *A61C 17/22* | (2006.01) | |
| *A46B 9/02* | (2006.01) | |
| *A46B 9/06* | (2006.01) | |

(52) U.S. Cl.
CPC ... *A46B 7/06* (2013.01); *A46B 3/00* (2013.01); *A46B 3/005* (2013.01); *A46B 9/028* (2013.01); *A46B 9/04* (2013.01); *A46B 9/06* (2013.01); *A61C 17/222* (2013.01); *A46B 2200/1066* (2013.01); *A46B 9/08* (2013.01); *A46B 13/02* (2013.01)

(58) Field of Classification Search
CPC ............. A46B 7/06; A46B 9/08; A46B 13/02
USPC ................................................. 15/167.1, 187
See application file for complete search history.

(56) References Cited

U.S. PATENT DOCUMENTS

| | | | | | |
|---|---|---|---|---|---|
| 1,725,852 | A | * | 8/1929 | Cressler | 15/167.1 |
| 3,128,487 | A | * | 4/1964 | Vallis | 15/176.1 |
| 3,174,174 | A | * | 3/1965 | Dengler | 401/25 |
| 8,033,287 | B2 | * | 10/2011 | Cullup | 132/309 |

FOREIGN PATENT DOCUMENTS

| | | |
|---|---|---|
| GB | 214701 A | 4/1924 |
| WO | 9827846 A1 | 7/1998 |

* cited by examiner

*Primary Examiner* — Randall Chin

(57) ABSTRACT

The toothbrush includes a brushhead (24) having a multi-layer bristle field assembly (30), which includes alternate thin base layers (32) and thin bristle layers (34) which are bonded together to form the bristle field assembly. The base layers provide support for the bristle field assembly while the bristle layers are configured to provide bristle elements therealong for brushing of the teeth.

9 Claims, 3 Drawing Sheets

TOOTHBRUSH WITH A BRISTLE FIELD WHICH COMPRISES A COMPOSITE OF LAYERS OF BASE AND BRISTLE COMPONENTS

CROSS-REFERENCE TO PRIOR APPLICATIONS

This application is the U.S. National Phase application under 35 U.S.C. §371 of International Application No. PCT/IB2012/057755, filed on Dec. 27, 2012, which claims the benefit of U.S. Provisional Patent Application No. 61/580,354, filed on Dec. 27, 2011. These applications are hereby incorporated by reference herein.

This invention relates generally to toothbrushes, and more specifically concerns a composite bristle field assembly for the brushhead portion of a toothbrush.

Toothbrushes typically are a mass produced article, designed for the average consumer. The bristle fields may vary somewhat in bristle stiffness and configuration in various commercial embodiments, but the variety available cannot come close to accommodating custom bristle fields to meet an individual user's requirements. This lack of custom capability results in some compromise in brushing efficiency and effectiveness for most consumers. There is thus a need for toothbrushes with custom bristle field configurations/patterns, both for manual and power toothbrushes, which are designed to accommodate an individual's particular brushing habits, particular oral geometry or current oral health conditions. This will improve the effectiveness of brushing. Brushing habits can include brushing force, grip, brushing motion, etc., while oral geometry issues can include misaligned teeth, different teeth size and shape of the dental arch and oral health conditions can include localized gingivitis, teeth sensitivity, and plaque and/or tartar production.

Customized bristle field arrangements to meet such individual needs has heretofore been not feasible because of the high cost of manufacture and/or the inability to actually produce custom toothbrushes.

The present bristle field arrangement is based on a composite structure arrangement which permits customization of a toothbrush to meet an individual's specific requirements.

The present toothbrush, with a brushhead having a bristle field assembly, comprises: a toothbrush handle; a brushhead assembly having a bristle field assembly at a distal end thereof, the bristle field assembly comprising a plurality of individual base layers comprising a material which is sufficiently stiff to provide support for the bristle field assembly; and a plurality of individual bristle layers positioned between the base layers, wherein the bristle layers are configured to form individual bristle elements for brushing teeth, wherein the base layers and bristle layers are bonded together to form a bristle field assembly.

Also, the present brushhead assembly, for use with a toothbrush, which includes a handle, comprises: a neck portion which extends from or is part of the toothbrush handle; a bristle field assembly at a distal end of the neck portion, comprising a plurality of individual base layers which are configured and arranged to provide support for the bristle field assembly; and a plurality of individual bristle layers positioned between the base layers, wherein the bristle layers are configured to form individual bristle elements along the bristle layer for brushing teeth, wherein the base layers and the bristle layers are bonded together to form the bristle field assembly.

Figure 1:
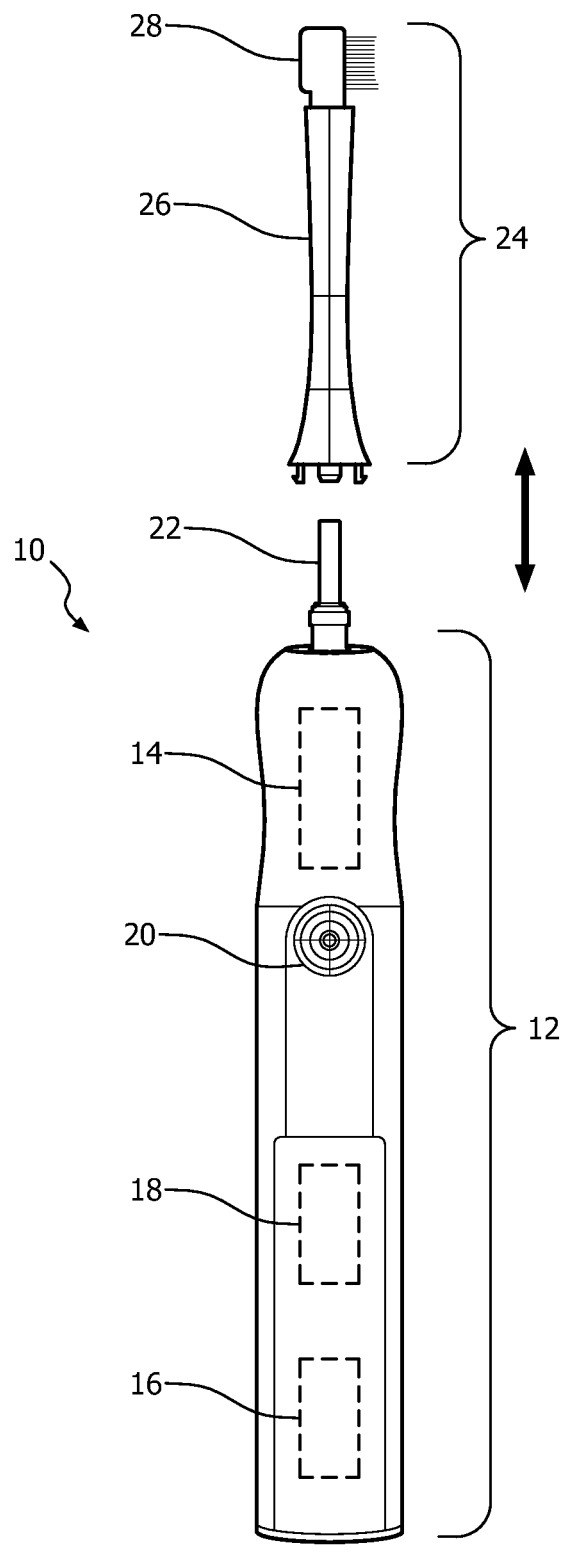
FIG. 1 is an elevational view showing a power toothbrush handle and a portion of the brushhead for the toothbrush.

FIG. 1 shows a typical power toothbrush with which the brushhead with the present bristle field assembly can be used. It should be understood, however, that the brushhead with the new bristle field assembly could be used with a manual toothbrush as well. The power toothbrush shown generally at 10 includes a handle portion 12. Within handle 12 is a driver assembly 14, a rechargeable battery 16 and a microcontroller 18. The toothbrush is controlled by an on/off button 20. The driver assembly 14, which is generalized, moves a driveshaft 22. The toothbrush also includes a brushhead portion 24 which includes a neck region 26 and a bristle field assembly at the distal end thereof, represented only in block form 28 in FIG. 1. The driveshaft 22 can produce various driving motions for the brushhead, including a partial rotation or a longitudinal motion, among others, to produce cleansing of the teeth by the bristle field. The power toothbrush in FIG. 1 is by way of example only and does not limit the scope of the brushhead portion. The bristle field assembly, which is the subject of the present application, is shown in detail in FIG. 2.

Figure 2:
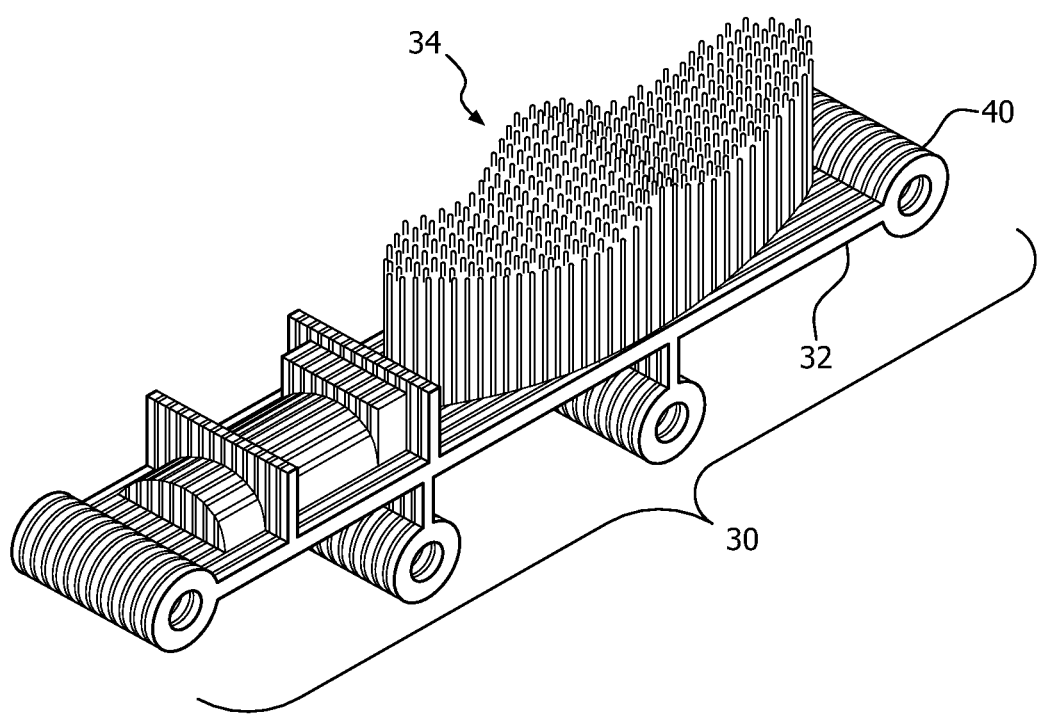
FIG. 2 is a perspective view showing the present multi-layer bristle field assembly, with alignment elements.

FIG. 2 shows the bristle field assembly 30 of the present invention which provides a custom toothbrush capability. The bristle field assembly 30 in general comprises two alternate pluralities of thin material layers, with the layers in one plurality of layers so configured and comprising such a material to form a sufficiently stiff base portion of the bristle field assembly that it serves as a support for the entire bristle field assembly, while the layers in the alternate plurality of layers comprise a more flexible material and are each configured/cut to define a plurality of individual bristle elements therealong, characterized to accomplish the cleaning of the teeth without discomfort to the user. FIG. 2 shows a completed bristle field assembly 30 following stacked construction of the separate pluralities of alternating base 32 and bristle 34 layers sufficient in number to form a bristle field to accomplish effective brushing of the teeth of a user.

Figure 3:
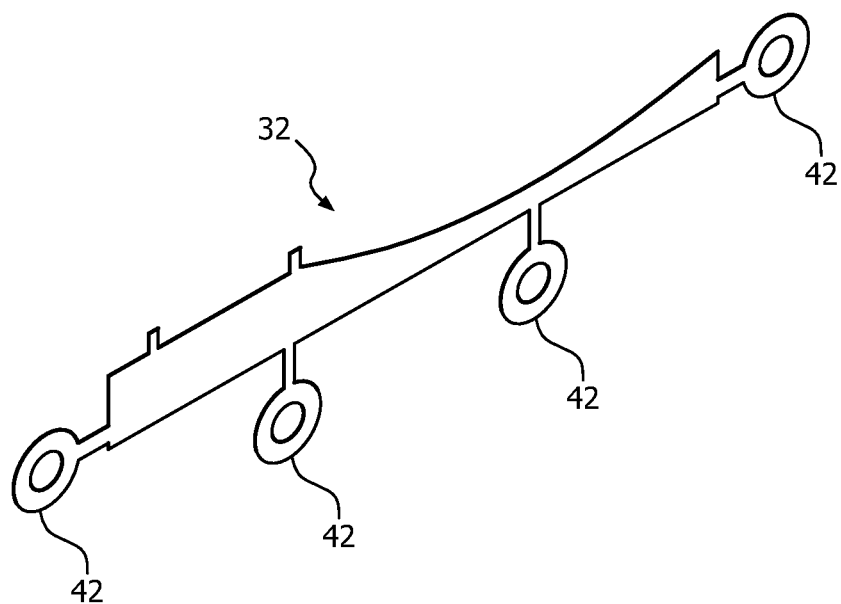
FIG. 3 is a perspective view showing a single base layer for the bristle field assembly, with alignment elements.

In the embodiment shown, base layers, one of which is shown in FIG. 3, are identified at 32-32 and for example comprise a PET (polyethylene terephthalate) material, with a preferred thickness of approximately 0.5 mm. Other materials of similar stiffness can be used. The plurality of alternating base layers provide the base support for the entire bristle field, sometimes referred to as a bristle base member in conventional brushheads. The material must be sufficiently stiff to support the bristle field as the brushhead is moved for brushing action, either by the user, such as in a manual toothbrush, or by the action of a power toothbrush. Typically, but not necessarily, base layers 32-32 are sufficiently thick and stiff that the adhesive which is used to bond the various layers together is applied to both sides of the base layers instead of both the base layers and the bristle layers.

Figure 4:
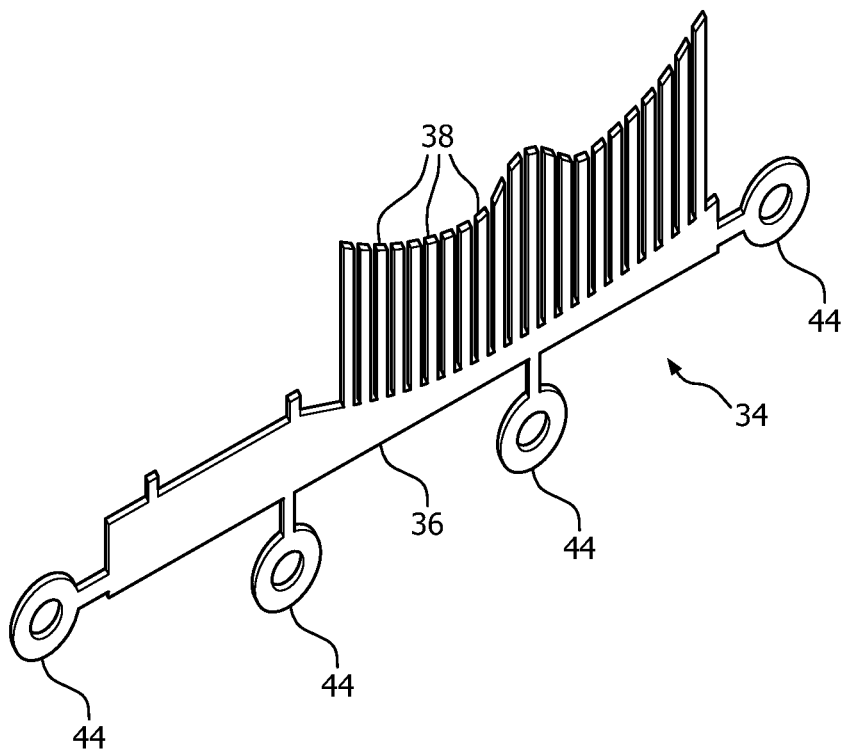
FIG. 4 is a perspective view of a single bristle layer for the bristle field assembly, with alignment elements.

The bristle layers, shown at 34-34 in FIG. 2 and singly in FIG. 4, comprise in the embodiment shown a TPE (thermoplastic elastomer) with a preferred thickness of 0.25 mm. Again, this material must be sufficiently flexible to provide good brushing action after each layer has been cut to form the individual bristles 38-38, which extend from remaining bottom portion 36.

The PET base material layers 32-32 are typically in the range of 0.1-0.75 mm thick, while the TPE bristle layers are in the range of 0.05-0.25 mm thick. The base and bristle layers are bonded together by an adhesive, typically alternately, to form the bristle field assembly, which can be applied on opposing sides of each base layer in the embodiment shown. The adhesive, which is shown at 40, can also be applied to both the base layers and the bristle layers to form the stack or layers. In the embodiment shown, the adhesive is a polyethylene glue, approximately 0.025 mm thick, although other adhesives can be used.

FIGS. 3 and 4 show the individual base and bristle layers in more detail. A single base layer 32 in FIG. 3 is shown with alignment elements 42-42, and generally is fairly short in height, approximately 5 mm. FIG. 4 shows a single bristle layer 34, which in the embodiment shown, is approximately 20 mm long, with the individual bristle elements 38-38 therealong. The bristle elements can vary in length, typically in the range of 3-10 mm, as well as trim configuration. Bristle layers 34 include alignment elements 44-44.

The base layers and the bristle layers can be produced by various known and available manufacturing techniques. One possible manufacturing technique is by laser cutting; water jet cutting machinery can also be used. The layers are cut individually in the desired configuration, including forming the individual bristles in the bristle layer as shown in FIG. 4 by cutting from the upper edge of the uncut layer down to a remaining bottom portion 36. The upper edge is cut to the desired trim configuration. The base and bristle layers are then bonded together to form the entire bristle field assembly.

Typically, the completed bristle field assembly will have a base outline similar to conventional bristle fields, approximately 20 mm long by 10 mm wide. In construction of the present bristle field assembly, the individual layers are positioned by their alignment elements, such as shown in FIGS. 3 and 4, although they could be located by other arrangements, such as pick and place technology. Further, although the bonding of the individual layers is accomplished with an adhesive in the embodiment shown, other bonding means could be used, including RF technology, ultrasonic or other means. The resulting stacked and bonded bristle field assembly is shown in FIG. 2. The alignment portions of the structure of FIG. 2 are then removed and the resulting assembly connected to the distal end of neck region 26 of the brushhead.

The bristle layers may vary in material to accommodate custom requirements of individual bristle fields. The bristle layers may vary in thickness and in stiffness, again depending upon the custom requirements of an individual bristle field. The completed brushhead can be a part of a power toothbrush, where it is typically replaceable, or alternatively, it could be part of a manual toothbrush. The brushhead in the manual toothbrush could also be replaceable.

The present bristle field assembly is advantageous, as indicated above, since it permits a wide range of customization possibilities, to meet individual needs, at a reasonable cost. In the overall process to produce a custom bristle field assembly and brushhead, a digital scan is first made of a user's particular oral geometry. Such digital scanning is well known, and there are several devices and techniques which are available to provide a suitable digital oral scan. The resulting scan data is then used to control a laser cutter or other cutting technology to produce the pluralities of base layers and bristle layers. The layers, as disclosed above, are stacked using the alignment elements, and then bonded to form the custom bristle field. The resulting toothbrush is thus matched to the particular oral needs of an individual user.

Although a preferred embodiment of the invention has been disclosed for purposes of illustration, it should be understood that various changes, modifications and substitutions may be incorporated in the embodiment without departing from the spirit of the invention which is defined by the claims which follow:

The invention claimed is:

1. A power toothbrush comprising:
    a toothbrush handle;
    a brushhead assembly having a bristle field assembly at a distal end thereof, the bristle field assembly comprising a plurality of individual base layers comprising a material which is sufficiently stiff to provide support for the bristle field assembly;
    a drive assembly to move the brushhead assembly in operation in order to accomplish the brushing action of the bristle field assembly; and
    a plurality of individual bristle layers positioned between the base layers, wherein the bristle layers comprise a different material than the base layer material, the material being flexible and the bristle layers varying individually in stiffness and/or bristle configuration in accordance with a preset pattern, the bristle layers being configured, including a thickness, to form individual bristle elements to produce effective brushing of teeth, wherein the base layers and bristle layers are bonded together to form the bristle field assembly.

2. The toothbrush of claim 1, wherein the base layers comprise a thermoplastic material having a thickness in the range of 0.1-0.75 mm, and wherein the bristle layers comprise a flexible material capable of brushing teeth without harm to surrounding tissues, with a thickness in the range of 0.05-0.25 mm.

3. The toothbrush of claim 1, wherein the bristle elements have a length approximately in the range of 3-10 mm.

4. The toothbrush of claim 1, wherein the bristle layers alternate with the base layers.

5. The toothbrush of claim 1, wherein the bristle field assembly has a length and width similar to a conventional bristle field.

6. A brushhead assembly for use with a toothbrush, comprising:
    a neck portion which extends from or is part of a toothbrush handle portion of the toothbrush;
    a bristle field assembly at a distal end of the neck portion, comprising a plurality of individual base layers which comprise a material which is sufficiently stiff and configured and arranged to provide support for the bristle field assembly; and
    a plurality of individual bristle layers positioned between the base layers, wherein the bristle layers comprise a different material from that of the base layer, the material being sufficiently flexible and the bristle layers varying individually in length and/or bristle element configuration in accordance with a preselected custom pattern, the bristle layers being configured, including a thickness, to form individual bristle elements to produce effective brushing of teeth, wherein the base layers and the bristle layers are bonded together to form the bristle field assembly.

7. The brushhead assembly of claim 6, wherein the bristle layers alternate with the base layers.

8. The brushhead assembly of claim 6, wherein the bristle field assembly has a width and length similar to a conventional bristle field.

9. The brushhead assembly of claim 6, wherein the bristle elements have a length approximately in the range of 3-10 mm.

\* \* \* \* \*